(12) United States Patent
Huber et al.

(10) Patent No.: US 6,706,868 B2
(45) Date of Patent: Mar. 16, 2004

(54) QUIESCENT CELL DIPEPTIDYL PEPTIDASE: A NOVEL CYTOPLASMIC SERINE PROTEASE

(75) Inventors: Brigitte T. Huber, Cambridge, MA (US); Robert H. Underwood, Quincy, MA (US)

(73) Assignee: The Trustees of Tufts University, Boston, MA (US)

( * ) Notice: Subject to any disclaimer, the term of this patent is extended or adjusted under 35 U.S.C. 154(b) by 0 days.

(21) Appl. No.: 10/233,745

(22) Filed: Sep. 3, 2002

(65) Prior Publication Data

US 2003/0027282 A1 Feb. 6, 2003

Related U.S. Application Data

(60) Division of application No. 09/388,413, filed on Sep. 1, 1999, now Pat. No. 6,485,955, which is a continuation-in-part of application No. 08/944,265, filed on Oct. 6, 1997, now abandoned.

(51) Int. Cl.[7] .............................................. C07H 21/04
(52) U.S. Cl. ..................................................... 536/23.2
(58) Field of Search ..................... 536/23.2; 435/252.33, 435/320.1, 69.1

(56) References Cited

U.S. PATENT DOCUMENTS 6,040,145 A    3/2000   Huber

FOREIGN PATENT DOCUMENTS

WO    WO 01/00812 A2    1/2001

OTHER PUBLICATIONS

Wallace et al in Methods Enzymol 152: 432–439, 1987.*

Kabcenell et al., "Mechanism of Action of Peptide Inhibitors of CD26 in T Cell Activation: Evidence Against a Direct Effect on Dipeptidyl Peptidase IV" Keystone Meetings pp. 20–26 (Mar. 1996).

Tan et al., J. Biol. Chem., 268 (22):16631–16638 (1993).

Duke–Cohan, et al., J. Biol. Chem., 270 (23):14107–14114 (1995).

Duke–Cohan, et al., J. Immunol., 156 (5):1714–1721 (1996).

Kahne, et al., Cellular Immunology, 170 (1):63–70 (1996).

* cited by examiner

Primary Examiner—Christina Chan
Assistant Examiner—Phuong N. Huynh
(74) Attorney, Agent, or Firm—Nixon Peabody LLP (57) ABSTRACT

Disclosed herein are the cDNA and polypeptide sequences of a novel cytoplasmic post-prolyl dipeptidase, QPP. QPP is expressed in T-cells and in neurons, and functions to protect quiescent cells from apoptotic death. Therefore, QPP can be used as a therapeutic to inhibit apoptotic cell death and as a target in screening for compounds that modulate cell death.

1 Claim, 7 Drawing Sheets

Asn Ala Phe Thr Val Leu Ala Met Met Asp Tyr Pro Tyr (SEQ ID NO 1)

Asp Leu Phe Leu Gln Gly Ala Tyr Asp Thr Val Arg (SEQ ID NO 2)

Leu Asp His Phe Asn Phe Glu Arg (SEQ ID NO 3)

Asp Val Thr Ala Asp Phe Glu Gly Gln Ser Pro Lys (SEQ ID NO 4)

*FIG. 1*

NUCLEIC ACID (SEQ ID NO 5); AMINO ACID (SEQ ID NO 6)

```
atg ggc tcc gct ccc tgg gcc ccg gtc ctg ctg ctg gcg ctc ggg ctg     48
Met Gly Ser Ala Pro Trp Ala Pro Val Leu Leu Leu Ala Leu Gly Leu
 1               5                  10                  15 cgc ctc cag gcg ggg gcc cgc agg gcc ccg gac ccc ggc ttc cag          96
Arg Leu Gln Ala Gly Ala Arg Arg Ala Pro Asp Pro Gly Phe Gln
            20                  25                  30 gag cgc ttc ttc cag cag cgt ctg gac cac ttc aac ttc gag cgc ttc    144
Glu Arg Phe Phe Gln Gln Arg Leu Asp His Phe Asn Phe Glu Arg Phe
        35                  40                  45 ggc aac aag acc ttc ccc cag cgc ttc ctg gtg tcg gac agg ttc tgg    192
Gly Asn Lys Thr Phe Pro Gln Arg Phe Leu Val Ser Asp Arg Phe Trp
 50                  55                  60 gtc cgg ggc gag ggg ccc acc ttc tac act ggg aac gag ggc gac        240
Val Arg Gly Glu Gly Pro Thr Phe Tyr Thr Gly Asn Glu Gly Asp
 65                  70                  75              80 gtg tgg gcc ttc gcc aac aac tcg ggc ttc gtc gcg gag ctg gcg gcc    288
Val Trp Ala Phe Ala Asn Asn Ser Gly Phe Val Ala Glu Leu Ala Ala
                85                  90                  95
```

*FIG. 2A*

```
gag cgg ggg gct cta ctg gtc ttc gcg gag cac cgc tac tac ggg aag    336
Glu Arg Gly Ala Leu Leu Val Phe Ala Glu His Arg Tyr Tyr Gly Lys
            100                 105                 110 tcg ctg ccg ttc ggt gcg cag tcc acg cag cgc ggg cac acg gag ctg    384
Ser Leu Pro Phe Gly Ala Gln Ser Thr Gln Arg Gly His Thr Glu Leu
        115                 120                 125 ctg acg gtg gag cag gcc ctg gca ttc gac gcc ctg ctc cgc gcg        432
Leu Thr Val Glu Gln Ala Leu Ala Phe Asp Ala Leu Leu Arg Ala
    130                 135                 140 cta cga cgc gac ctc ggg gcc cag gat gcc ccc atc gcc ttc ggt        480
Leu Arg Arg Asp Leu Gly Ala Gln Asp Ala Pro Ile Ala Phe Gly
145                 150                 155                 160 gga agt tat ggg ggg atg ctc agt gcc tac ctg agg atg aag tat ccc    528
Gly Ser Tyr Gly Gly Met Leu Ser Ala Tyr Leu Arg Met Lys Tyr Pro
                165                 170                 175 cac ctg gtg gcg ggg gcg ctg gcg gcg ctg gcg ccc gtt cta gct gtg    576
His Leu Val Ala Gly Ala Leu Ala Ala Ser Ala Pro Val Leu Ala Val
            180                 185                 190
```

*FIG. 2B*

```
gca ggc ctc ggc gac tcc aac cag ttc cgg gac gtc acg gcg gac                    624
Ala Gly Leu Gly Asp Ser Asn Gln Phe Arg Asp Val Thr Ala Asp
195             200             205 ttt gag ggc cag agt ccc aaa tgc acc cag ggt gtg cgg gaa gcg ttc                672
Phe Glu Gly Gln Ser Pro Lys Cys Thr Gln Gly Val Arg Glu Ala Phe
        210             215             220 cga cag atc aag gac ttg cta cag gga gcc tac gac acg gtc cgc                    720
Arg Gln Ile Lys Asp Leu Phe Leu Gln Gly Ala Tyr Asp Thr Val Arg
225             230             235             240 tgg gag ttc ggc acc tgc cag ccg ctg tca gac aag gac ctg acc                    768
Trp Glu Phe Gly Thr Cys Gln Pro Leu Ser Asp Lys Asp Leu Thr
            245             250             255 cag ctc ttc atg ttc gcc cgg aat gcc ttc acc gtg ctg gcc atg atg               816
Gln Leu Phe Met Phe Ala Arg Asn Ala Phe Thr Val Leu Ala Met Met
        260             265             270 gac tac ccc act gac ttc ctg ggt ccc ctc cct gcc aac ccc                        864
Asp Tyr Pro Thr Asp Phe Leu Gly Pro Leu Pro Ala Asn Pro
275             280             285
```

FIG. 2C

```
gtc aag gtg ggc tgt gat cgg ctg agt gag gcc cag agg atc acg    912
Val Lys Val Gly Cys Asp Arg Leu Ser Glu Ala Gln Arg Ile Thr
290              295              300 ggg ctg cga gca ctg gca ggg ctg gtc tac aac gcc tcg ggc tcc gag    960
Gly Leu Arg Ala Leu Ala Gly Leu Val Tyr Asn Ala Ser Gly Ser Glu
305              310              315 cac tgc tac gac atc tac cgg ctc tac cac agc tgt gct gac ccc act   1008
His Cys Tyr Asp Ile Tyr Arg Leu Tyr His Ser Cys Ala Asp Pro Thr
        325              330              335 ggc tgc ggc acc ggc ccc gac gcc agg gcc tgg gac tac cag gcc tgc   1056
Gly Cys Gly Thr Gly Pro Asp Ala Arg Ala Trp Asp Tyr Gln Ala Cys
340              345              350 acc gag atc aac ctg acc ttc gcc agc aac aat gtg acc gat atg ttc   1104
Thr Glu Ile Asn Leu Thr Phe Ala Ser Asn Asn Val Thr Asp Met Phe
        355              360              365 ccg gac ctg ccc ttc act gac gag ctc cgc cag cgg tac tgc ctg gac   1152
Pro Asp Leu Pro Phe Thr Asp Glu Leu Arg Gln Arg Tyr Cys Leu Asp
370              375              380
```

FIG. 2D

```
acc tgg ggc gtg tgg ccc gac tgg ctg ctg acc agc ttc tgg      1200
Thr Trp Gly Val Trp Pro Asp Trp Leu Leu Thr Ser Phe Trp
385                 390                 395                 400 ggg ggt gat ctc aga gcc gcc agc aac atc ttc tcc aac ggg aac  1248
Gly Gly Asp Leu Arg Ala Ala Ser Asn Ile Phe Ser Asn Gly Asn
        405                 410                 415 ctg gac ccc tgg gca ggg ggc att cgg agg aac ctg agt gcc tca  1296
Leu Asp Pro Trp Ala Gly Gly Ile Arg Arg Asn Leu Ser Ala Ser
420                 425                 430 gtc atc gcc gtc acc atc cag ggg gga gcg cac cac ctc gac ctc aga  1344
Val Ile Ala Val Thr Ile Gln Gly Gly Ala His His Leu Asp Leu Arg
435                 440                 445 gcc tcc cac cca gaa gat cct gct tcc gtg gtt gag gcg cgg aag ctg  1392
Ala Ser His Pro Glu Asp Pro Ala Ser Val Val Glu Ala Arg Lys Leu
450                 455                 460 gag gcc acc atc atc ggc gag tgg gta aag gca gcc agg cgt gag cag  1440
Glu Ala Thr Ile Ile Gly Glu Trp Val Lys Ala Ala Arg Arg Glu Gln
465                 470                 475                 480
```

FIG. 2E

```
cag cca gct ctg cgt ggg ggg ccc aga ctc ctc tga gca cag gac   1488
Gln Pro Ala Leu Arg Gly Pro Arg Leu Ser Leu *   Ala Gln Asp
            485                 490       (SEQ ID NO:6)  495 tgg agg ggt ctc aag gct cct cat gga gtg ggg gct tca ctc aag cag   1536
Trp Arg Gly Leu Lys Ala Pro His Gly Val Gly Ala Ser Leu Lys Gln
            500                 505                 510 ctg gcg gca gag gga agg ggc tga ata aac gcc tgg agg cct ggc aaa   1584
Leu Ala Ala Glu Gly Arg Gly *   Ile Asn Ala Trp Arg Pro Gly Lys
            515      (SEQ ID NO:7)  520                 525 aaa aaa aaa aaa aaa aaa aaa aaa aaa aaa aa   1619
Lys Lys Lys Lys Lys Lys Lys Lys Lys Lys
            530                 535   (SEQ ID NO:8)
```

FIG. 2F

QUIESCENT CELL DIPEPTIDYL PEPTIDASE: A NOVEL CYTOPLASMIC SERINE PROTEASE

CROSS-REFERENCE TO RELATED APPLICATION

This application is a Divisional of U.S. Ser. No. 09/388,413 filed on Sep. 1, 1999 which is now U.S. Pat. No. 6,485,955, which claims priority benefit of Continuation-in-Part of U.S. Ser. No. 08/944,265 filed Oct. 6, 1997 now abandoned.

BACKGROUND OF THE INVENTION

This invention relates to a novel cytoplasmic post-prolyl dipeptidase, and its role in regulating apoptosis, or programmed cell death (PCD).

Apoptosis is a physiological form of cell death, and it shapes a number of diverse biological processes, such as development and homeostasis. It occurs in response to diverse stimuli which fall into two categories. The first is activation-induced cell death following specific stimulation; and the second is death by neglect after withdrawal of a life-promoting stimulation, such as a growth factor, serum or cell-cell contact. While these two types of PCD take place under very different circumstances, both depend on the activation of caspases, a family of cysteine proteases which are present in the cytoplasm of cells as inactive proenzymes.

Apoptotic stimuli lead to the activation of certain caspases by specific proteolytic cleavage, enabling them to activate other caspases through a proteolytic cascade, which eventually leads to cell death. Studies of activation-induced cell death through the Fas/TNF receptors have implicated the death effector domain-containing protease FLICE (caspase 8) in the initiation of the caspase cascade. However, while most cells contain all the components of the apoptotic machinery, and are susceptible to PCD by neglect, no caspase-cascade regulator induced under these conditions, has been identified.

With respect to apoptosis in the nervous system, recent studies have shown that neuronal cell death resulting from degeneration or trauma occurs by the process of apoptosis, the biochemical hallmarks of which include cytolemmal membrane blebbing, cell soma shrinkage, chromatin condensation, and DNA laddering. Thus, given the role of apoptosis in neural degeneration, it would be highly desirable to have a process for identifying compounds that modulate this apoptosis. Such compounds could be effective as therapeutic agents in the treatment or prevention of neural conditions associated with inappropriate neural degeneration. However, one of the fundamental technological problems associated with the identification of these compounds is the lack of suitable targets to use in screening for regulators of apoptosis. Thus, there is a need to identify new enzymatic targets as a first step in developing new therapeutic compounds.

SUMMARY OF THE INVENTION

We have discovered a novel, cytoplasmic post-prolyl dipeptidase, which has similarities to, but is distinct from, the membrane-bound T-cell serine protease CD26. This enzyme is expressed in quiescent, non-cycling T-cells and in neurons, and is called quiescent cell post-prolyl dipeptidase (QPP; previously termed DPIVb).

In a first aspect, the invention features a substantially pure, recombinant quiescent cell post-prolyl dipeptidase polypeptide (QPP). wherein the polypeptide inhibits quiescent cells from undergoing apoptosis. Preferably, the polypeptide comprises the amino acid sequence of SEQ ID NO 6.

In a second and related aspect, the invention features a substantially pure nucleic acid molecule encoding a QPP polypeptide, wherein the nucleic acid sequence comprises SEQ ID NO 5, or a sequence that is complementary to a sequence that hybridizes to SEQ ID NO 5 under stringent hybridization conditions encoding a QPP polypeptide, or encodes a polypeptide of SEQ ID NO 6.

The invention also features a host cell, for example, yeast, E. coli, Chinese hamster ovary (CHO), or fibroblast, transformed or transfected with a transgene that includes a nucleic acid molecule encoding a QPP polypeptide, wherein the nucleic acid molecule is operably linked to a regulatory sequence, and wherein the nucleic acid sequence comprises SEQ ID NO 5, or a sequence that is complementary to a sequence that hybridizes to SEQ ID NO 5 under stringent hybridization conditions, or encodes a polypeptide of SEQ ID NO 6.

In a related aspect, the invention features a method of producing a QPP polypeptide including transforming or transfecting a cell with a nucleic acid molecule encoding a QPP polypeptide, wherein the nucleic acid molecule is operably linked to a regulatory sequence, and further wherein the nucleic acid sequence comprises SEQ ID NO 5, or a sequence that is complementary to a sequence that hybridizes to SEQ ID NO 5 under stringent hybridization conditions, or encodes a polypeptide of SEQ ID NO 6; culturing the cell under conditions for expressing the nucleic acid; and isolating the QPP polypeptide.

The purified QPP sequences of the invention have a number of utilities. The invention features methods for: 1) identifying a therapeutic candidate compound that modulates a QPP effect in quiescent cells, which includes contacting a recombinant QPP polypeptide, preferably, the QPP polypeptide of SEQ ID NO 6, or a transformed or transfected cell encoding and expressing a recombinant QPP polypeptide, with the compound and measuring QPP biological activity; 2) inhibiting apoptosis in a quiescent cell, which includes contacting the cell with a recombinant QPP polypeptide, preferably, the QPP polypeptide of SEQ ID NO 6, in an amount sufficient to protect the cell from death when an apoptosis stimulus is administered; and 3) treating a mammal for a condition related to quiescent cell death, that includes administering to the mammal a recombinant QPP polypeptide, preferably, the QPP polypeptide of SEQ ID NO 6, in an amount sufficient to inhibit the cell death. Preferably, the condition is a neurodegenerative disorder or an immune system disorder, and the QPP polypeptide may be administered by transplanting a host cell into the mammal, wherein the host cell is ex vivo transfected with a transgene comprising a nucleic acid molecule encoding a QPP polypeptide, wherein the nucleic acid molecule is operably linked to a regulatory sequence and is expressed in the transplanted host cell.

The recombinant QPP sequences can also be used to make antibodies (polyclonal, monoclonal, or recombinant) using conventional methods, involving immunization of, e.g., rabbits, mice, or human volunteers. The antibodies can be used in standard ELISA assays to measure QPP levels in patients being tested for diseases which potentially involve increased or decreased QPP levels; for example, HIV patients, who have lost QPP-containing T-cells, will exhibit decreased QPP levels, with the QPP concentration being diagnostic of the stage of the disease. Generally, because QPP is a cytoplasmic enzyme, the assay is carried out on peripheral blood lymphocyte samples which have first been treated to lyse T-cells to release the enzyme.

By "substantially pure" is meant a polypeptide or nucleic acid that has been separated from components which normally accompany it, or which accompany it upon recumbent expression. An enzyme is substantially pure when it is at least 60%, by weight, free from the proteins and naturally-occurring organic molecules with which it is naturally associated. Preferably, the preparation is at least 75%, more preferably, at least 90%, and most preferably, at least 99%, pure QPP by weight. Purity can be measured by any appropriate method, e.g., column chromatography, polyacrylamide gel electrophoresis, or by HPLC analysis.

By "apoptosis" is meant the process of programmed cell death wherein a dying cell displays a set of well-characterized biochemical hallmarks which include cytolemmal membrane blebbing, cell soma shrinkage, chromatin condensation, and DNA laddering.

By "stringent hybridization conditions" is meant incubation conditions that destabilize mismatched heteroduplexes. Conditions for high stringency hybridization, such as for PCR, Northern, Southern, in situ hybridization, or DNA sequencing, are described, for example, in F. Ausubel et al., *Current Protocols in Molecular Biology*, John Wiley & Sons, New York, N.Y., 1994.

By "transformed" or "transfected" cell is meant a cell in which foreign nucleic acid molecules have been introduced. Lipofection, DEAE-dextran-mediated transfection, microinjection, protoplast fusion, calcium phosphate precipitation, retroviral delivery, electroporation, and biolistic transformation are just a few of the methods known to those skilled in the art which may be used. For example, biolistic transformation is a method for introducing foreign molecules into a cell using velocity driven microprojectiles such as tungsten or gold particles. Such velocity-driven methods originate from pressure bursts which include, but are not limited to, helium-driven, air-driven, and gunpowder-driven techniques. Biolistic transformation may be applied to the transformation or transfection of a wide variety of cell types and intact tissues including, without limitation, intracellular organelles (e.g., and mitochondria and chloroplasts), bacteria, yeast, fungi, algae, animal tissue, and cultured cells.

By "apoptotic stimulus" is meant any chemical or physical treatment which initiates apoptosis as defined above. For example, nerve growth factor withdrawal, hypoxia, exposure to staurosporine, and cerebral ischemia are stimuli capable of inducing apoptosis in neurons.

The "quiescent cell" is meant a non-cycling cell in a non-replicative or resting state.

By "QPP effect" is meant QPP's VbP-sensitive protection against apoptosis in quiescent cells.

By "test compound" is meant a chemical, be it naturally-occurring or artificially-derived, that is surveyed for its ability to modulate cell death, by employing one of the assay methods described herein. Test compounds may include, for example, small molecules, peptides, polypeptides, synthesized organic molecules, naturally occurring organic molecules, nucleic acid molecules, and components thereof.

By "therapeutic candidate compound" is meant a compound that modulates a QPP effect, and is, therefore, a candidate for use as a therapeutic to inhibit cell death in quiescent cells.

By "measuring QPP biological activity" is meant analyzing the effect of a test compound, whether the effects be chemical or physical. The material being analyzed may be an animal, a cell, a lysate or extract derived from a cell, or a molecule derived from a cell. The analysis may be for the purpose of detecting a change in QPP biology such as altered RNA stability, altered protein stability, altered protein levels, altered enzymatic activity, or an altered rate of QPP-mediated apoptotic death. The means for analyzing may include, for example, antibody labeling, immunoprecipitation, substrate cleavage assays, and methods known to those skilled in the art for detecting nucleic acids.

By "modulates" is meant changing, either by decrease or increase.

By "operably linked" is meant that a gene and a regulatory sequence are connected in such a way as to permit expression of the gene product under the control of the regulatory sequence.

By a "transgene" is meant a nucleic acid sequence which is inserted by artifice into a cell and becomes a part of the genome of that cell and its progeny. Such a transgene may be partly or entirely heterologous to the cell.

Other features and advantages of the invention will be apparent from the following detailed description, and from the claims.

DETAILED DESCRIPTION

We have discovered that a novel polypeptide, QPP, isolated from T-cells in healthy individuals, is involved in the protection of T-cells from apoptosis. This cell death-related property of QPP was discovered during studies of T-cell survival during HIV infection. Our observations led us to hypothesize that the inhibition of QPP in HIV-infected individuals caused resistance to full T-cell activation, which further prevents differentiation into effector cells, and eventually leads to T-cell death. When not inhibited, QPP prevents this apoptosis in resting T-cells by blocking the catalytic activation of caspases. QPP's dipeptidase activity is present in the cytoplasm of a number of types of normal, resting human T-cells, e.g., CD4 cells and Jurkat cells. In addition to T-cells, QPP is also expressed in neurons.

QPP Discovery and Purification

The work leading up to the discovery of QPP began with the question of whether, in resting cells, the apoptotic machinery may be kept inactive by the basal activity of cellular enzymes. To find an answer, various enzymatic inhibitors were screened for their ability to trigger PCD in overnight cultures of freshly isolated peripheral blood mononuclear cells (PBMC).

1. VbP Causes Cell Death in Resting T Cells

We observed a striking increase in the number of dead cells in cultures containing the L-isomer of Val-boroPro (VbP), an inhibitor of dipeptidyl peptidase IV (DPPIV), compared to cultures containing media alone or the inactive D-isomer of the inhibitor, d-Val-d-boroPro—a toxicity control. Dead cells were apparent as early as 4 hours after the addition of the L-isomer of VbP, with maximal death occurring within 24 hours (about 70%). When subpopulations of PBMC were tested for susceptibility to VbP-induced death, we observed that $CD19_+$ B cells and $CD11b^+$ monocytes were resistant, while purified T-cells ($CD4^+/CD8^+$) showed greater sensitivity than whole PBMC. These results imply that the molecular target of VbP plays a role in T-cell survival. Surprisingly, activated PBMC are resistant to VbP-induced PCD, but regain sensitivity if maintained in culture until the cells return to a non-cycling phage ($G_0$).

2. Mechanisms of VbP-Induced Death

We first demonstrated that the death induced by VbP in resting T cells was caspase-dependent apoptosis and was independent of Fas and the proteosome pathway.

First, turning to caspase-mediated apoptosis, the appearance of phosphatidylserine (PS) on the outer leaflet of the plasma membrane is a caspase dependent characteristic of apoptotic cells. By using the PS binding protein FITC-annexin V, we detected a time-dependent increase in the amount of PS on the surface of cells treated with VbP, establishing that VbP induces apoptosis. The role of caspase in VbP-mediated PCD was confirmed, given that the general caspase inhibitor Z-VADfmk blocked VbP-mediated T-cell death.

To determine if other known mediators of activation-induced death were involved, we investigated Fas, the well defined and prototypic activation-induced death pathway of T-cells, and the proteosome pathway. Fas was studied using anti-Fas mAb M3, which prevents PCD by blocking Fas-FasL interactions. The proteosome pathway was investigated using lactacystin, an inhibitor of proteosome activity, which induces cell death through the disregulation of proteins necessary for cell cycle progression, and does not induce PCD in resting PBMD. Although these pathways typically affect activated cells, and PBMC are predominantly resting cells, we hypothesized that exposure to small molecule drugs like VbP might induce the expression of Fas ligand (FasL) or have other unanticipated effects that activate these pathways. However, neither the anti-Fas mAb M3 nor lactacystin had any effect on VbP-mediated death in non-cycling T-cells. (However, after activation, PBMC are susceptible to lactacystin-induced death.) These findings confirm that VbP-mediated PCD in resting cells proceeds through the caspase cascade and is independent of Fas-FasL interactions or a proteosome-mediated cell cycle block.

3. The VbP Target, QPP, is Pharmacologically Distinct from DPIV

VbP was designed to inhibit DPIV, a catalytic activity attributed to the surface memory T-cell antigen CD26. However, VbP has an additional target, given that VbP caused T-cell death to the same degree in both $CD26^+$ and $CD26^-$ resting T-cell subpopulations. Since VbP is a highly potent inhibitor of DPIV, the novel VbP target is an enzyme with substrate specificity similar to that of DPIV. Furthermore, peptidyl boronic acids, like VbP, are effective inhibitors of serine proteases, but do not inhibit cysteine proteases, indicating that the cytosolic enzyme responsible for AlaProAFC cleavage belongs to the serine class of proteases. Thus, we began to biochemically characterize the novel target by assaying cleavage of the DPIV substrate AlaProAFC.

First, membrane and cytosolic fractions were prepared from freshly isolated PBMC. The cytosolic preparation (110,000 g supernatant) contained a pH dependent Ala-ProAFC cleaving enzymatic activity. This activity is not the result of DPIV action, because CD26 (DPIV) fractionates with the membranes (110,000 g pellet). Optimal AlaProAFC cleavage occurred at pH 7.5, excluding lysosomal proteases as the source of this activity. The enzymatic activity was inhibited by VbP and was partially inhibited by high concentrations of benzamidine and the serine/cysteine protease active site titrants PMSF, TLCK, NEM and IAA, which most likely act as nonspecific alkylating agents at these high concentrations.

Because of the similar substrate specificities of the new cytoplasmic peptidase QPP and the known enzyme DPIV, we compared the inhibitory profile of QPP to DPIV. Several known DPIV peptidase inhibitors were tested on QPP: 1) VbP; 2) the fluoroolefin containing (Z)-Ala-[CF═C]-Pro-NHO-Bz($4NO_2$) (L-125); and 3) $NO_2$-Z-Lys-thiazolidide (Lys-thiaizolidide). In addition, another compound related to Lys-thiazolidide, $NO_2$-Z-Lys-piperidide (Lys-piperidide), which does not inhibit DPIV, was also tested. QPP inhibition was achieved with similar concentrations of VbP and Lys-thyazolidide, the most potent inhibitors of this activity. The related compound, Lys-piperidide, did inhibit QPP at higher concentrations than Lys-thiazolidide, and the DPIV inhibitor, L-125, did not inhibit QPP. Therefore, the differences in the inhibitory profiles of DPIV and the quiescent T-cell VbP target (QPP) verified that QPP is distinct from DPIV. Furthermore, QPP's role in the VbP-induced T-cell death was confirmed by the fact that the inhibitors' effects on QPP's cleaving activity closely correlated with the inhibitors' effects on PCD induction in PBMC cultures.

Given our functional and pharmacological data, QPP is established as a novel enzymatic inhibitor of the caspase cascade in quiescent T-cells, and is a target for the regulation of this pathway. In resting T-cells, the caspase cascade is kept inactive through the action of QPP; inhibition of QPP allows activation of the caspase cascade, leading to cell death. The implication of this model, that resting T cells are poised to die, is consistent with the notion that PCD is a constitutive program which must be suppressed. Resting T-cells seem to be the sole target of VbP-induced death in the PBMC population, despite the presence of similar peptidase activities in the cytoplasm of activated T-cells and other blood cells. Interestingly, we observed a 9-fold reduction of AlaProAFC specific cleaving activity in cytoplasmic extracts from PHA activated T-cell blasts compared to that of quiescent PBMC, suggesting that this activity is replaced by other inducible proteolytic activities upon cellular activation. Thus, we anticipate that QPP is the first identified member of a family of proteolytic activities which regulate the caspase cascade in quiescent cells.

Methods

Human PBMC were isolated from the blood of healthy donors by centrifugation on a Ficoll-Hypaque gradient using standard techniques. T-cells and monocytes were isolated by sorting on a Becton Dickinson FACStar plus flow cytometer using biotinyl-anti-CD4 plus biotinyl-anti-CDS (Leu2a plus Leu2b, Becton Dickinson) or anti-CD11b (44-biotin, Sigma), and phycoerythrin streptavidin, $CD26^+$ T cells were isolated by sorting with the anti-CD26 mAb 1F7 (C. Morimoto, Dana-Farber Cancer Inst.). B cells were isolated by selection with biotinyl-anti-CD19 mAb (D. Thorley Lawson, Tufts Univ.) And MACS microbeads (Miltenyi Biotec). Sorted cell populations were >90% pure. Cells were washed several times in PBS and resuspended in serum free AIM V medium (Gibco), and plated at $1-2\times10^5$ cells/well in 96 well flat-bottom plates. Enzyme inhibitors and mAb were added and the cells incubated for 18–24 hours in 5% $CO_2$ at 37 C. Cellular death was quantitated by staining the cells with 20 g/ml 7-amino actinomycin D (Sigma), hypotonic propidium iodide (Sigma), or FITC-annexin V (Southern Biotech Associates). Activated cells (PHA Blasts) were stimulated for 3 days with 5 g/ml phytohemagglutinin (PHA, Sigma). Long Term Cultured cells were cultured with PHA for 3 days, washed several times and cultured an additional 32 days without stimulating agents. Additional reagents: anti-FAS mAb M3 (D. Lynch, Immunex); Z-VADfmk (Enzyme System Products); lactacystin (E. J. Corey, Harvard Univ.); VbP, Lys-piperidide, Lys-thiazolidide (R. Snow and A. Kabcenell, Boehringer Ingelheim Pharmaceuticals), L-125 (J. Welch, State Univ. of N.Y., Albany).

Enzyme Characterization

Human PBMC ($430 \times 10^6$ cells) were isolated from 450 ml whole blood. Cells were resuspended in 7 ml ice cold lysis buffer (0.02 M Tris pH 7.8, 4 g/ml aprotinin, 8 g/ml leupeptin, 8 g/ml antipain) and held on ice 10 min before homogenization by 10 strokes of a Dounce homogenizer. EDTA was added to a final concentration of 5 mM, and the homogenate centrifuged at 1000 g for 10 min. at 4 C. The resulting supernatant was centrifuged at 45,000 g for 20 min. at 4 C. The 45,000 g supernatant was centrifuged at 110,000 g for 1 hour at 4 C, the 110,000 g supernatant was used as soluble cytoplasmic extract. The 45K and 110K pellets were combined, resuspended in 10 ml lysis buffer, and centrifuged at 110,000 g for 20 min. at 4 C. The resulting pellets were combined and resuspended in lysis buffer/1% Triton X-100 and used as the membrane preparation. Peptidase activity was measured by monitoring the 1 min. accumulation of the fluorescent product 7-amino-4-trifluoromethylcoumarin (AFC) liberated from the substrate AlaProAFC (Enzyme Systems Products), using a Perkin-Elmer fluorescence spectrophotometer (excitation 400 nm, emission 505 nm). The optimal pH for AlaProAFC cleavage was determined using: 0.05 M acetate pH 4.5, 5.0; 0.2 M piperazine pH 5.5, 0.05 M NaPhosphate pH 6.0, 6.5, 7.0; 0.05 M HEPES pH 7.5, 8.0, 0.02 M TRIS pH 8.5, 9.0; 0.05 M HEPES pH 7.5 was used for all subsequent enzymatic assays. The general protease inhibitors: PMSF, benzamidine, TLCK, aprotinin, leupeptin, IAA and NEM were purchased from Sigma. All reported catalytic rates are the average of 3 independent determinations.

We detected an enzymatic activity (cleavage of the substrate AlaProAFC) in the soluble fraction of CD26-Jurkat cells. The activity is inhibited by the DPIV inhibitors XaaboroPro (Bachovchin et al. U.S. Pat. No. 5,462,928, hereby incorporated by reference). However, the activity is distinct from DPIV based upon differential sensitivity to other inhibitors (thiazolidide, piperidide, PMSF). The activity is greatly reduced (more than 50%) at pH 5.5.

OPP Purification

We purified QPP from Jurkat cytoplasm. The following general scheme produces a 1000-fold purification of QPP with a 27% yield:

1. Jurkat cytoplasm (110,000 g supernatant);
2. Acid soluble fraction (0.05 M acetate pH 4.5);
3. Cation Exchange (SP); and
4. Gel filtration (Superdex 12).

In more detail, the above-outlined purification scheme is carried out as follows. First, Jurkat cells ($10^6$–$10^{11}$ cells) are grown and a cell pellet is obtained by centrifugation. The cell pellet is stored in frozen condition.

The frozen pellet is thawed by the addition of ice cold lysis buffer, in the amount of approximately 1 ml per 10 cells. The liquified material is homogenized with ten strokes of a Dounce homogenizer, and then clarified by centrifugation at 1500 g. The supernatant is removed, and reserved. The 1500 g pellet is resuspended in lysis buffer and homogenized with ten strokes of a Dounce homogenizer. Clarification is again carried out by centrifugation at 1500 g at 4 C.

The 1500 g supernatants are then combined, and EDTA is added to 5 mM. The resultant liquid is centrifuged at 75,000 g at 4 C for twenty minutes, and the supernatant is then removed and centrifuged at 110,000 g at 4 C, for 60 minutes. The resultant supernatant, containing the cytosolic extract, is the QPP activity-containing fraction on which the subsequent purification steps are carried out.

This procedure does not yield a homogeneous preparation, and attempts at further purification (ion exchange, affinity chromatography) resulted in the loss of nearly all protein in the sample, and recovery of very little activity.

To identify the component of this purified preparation responsible for XaaPro-cleaving activity, we established that diisopropylfluorophosphate (DFP) inhibits the activity in the SP purified fraction. An aliquot of the most pure preparation was then labeled with 3H-DFP and separated by SDS-PAGE. Radiofluorography of the dried gel revealed a specifically labeled protein of 60 kD. The corresponding band from a Coomassie stained gel contained purified QPP.

4. Novelty of QPP Confirmed by Sequencing; Cloning of QPP cDNA

Figure 1:
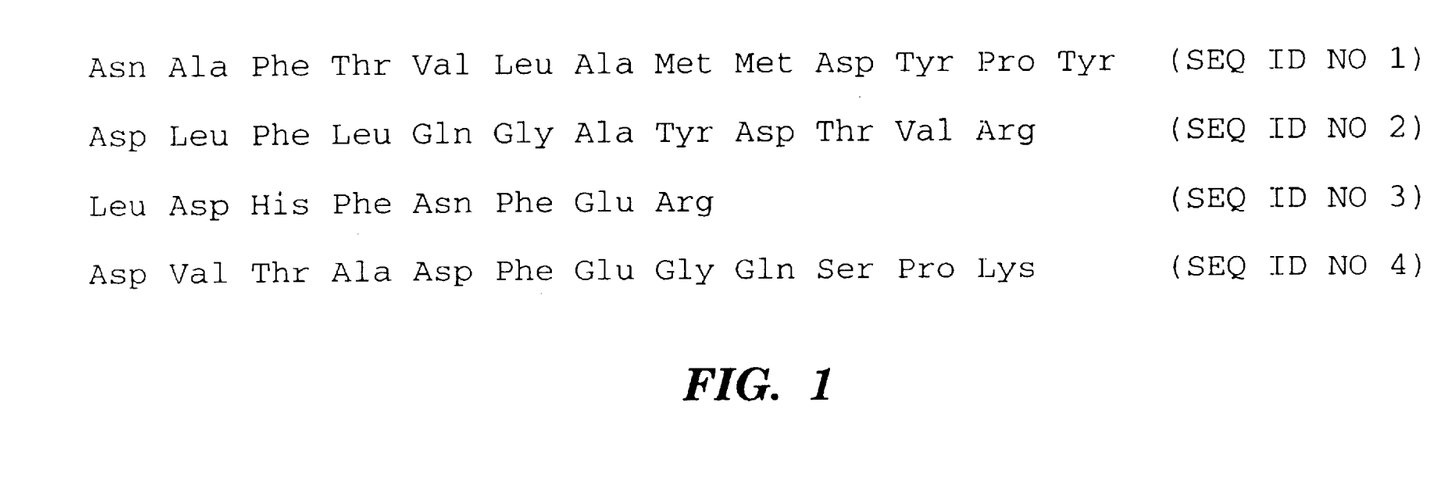
FIG. 1 shows the amino acid sequences of four peptide fragments of QPP following tryptic digestion (SEQ ID NOs 1–4).
Figure 2A:
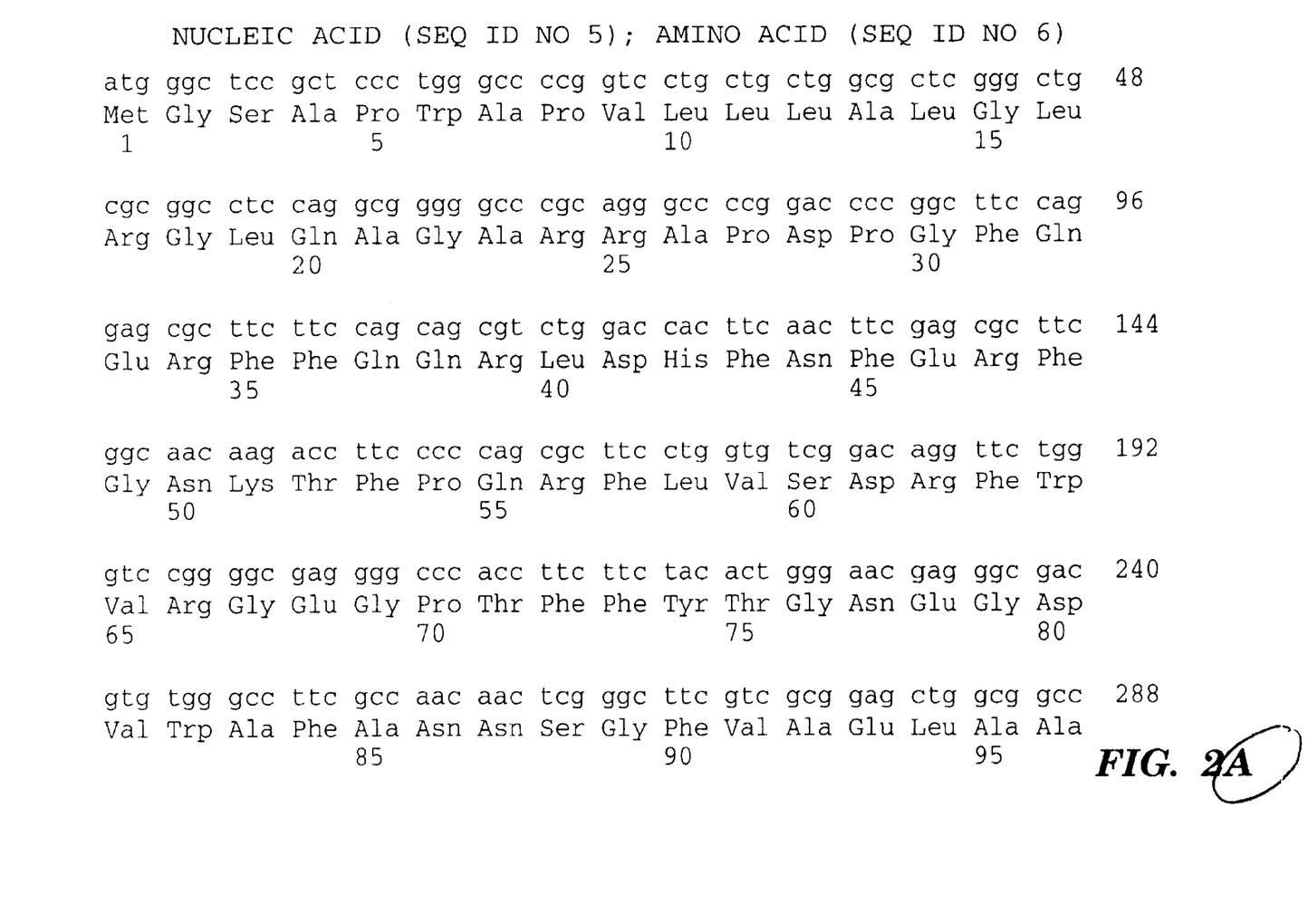
FIGS. 2A–2F show the QPP cDNA sequence (SEQ ID NO 5), amino acid sequence 1–492 (SEQ ID NO 6), amino acid sequence 493–518 (SEQ ID NO 7), and amino acid sequence 519–537 (SEQ ID NO 8).
Figure 2B:
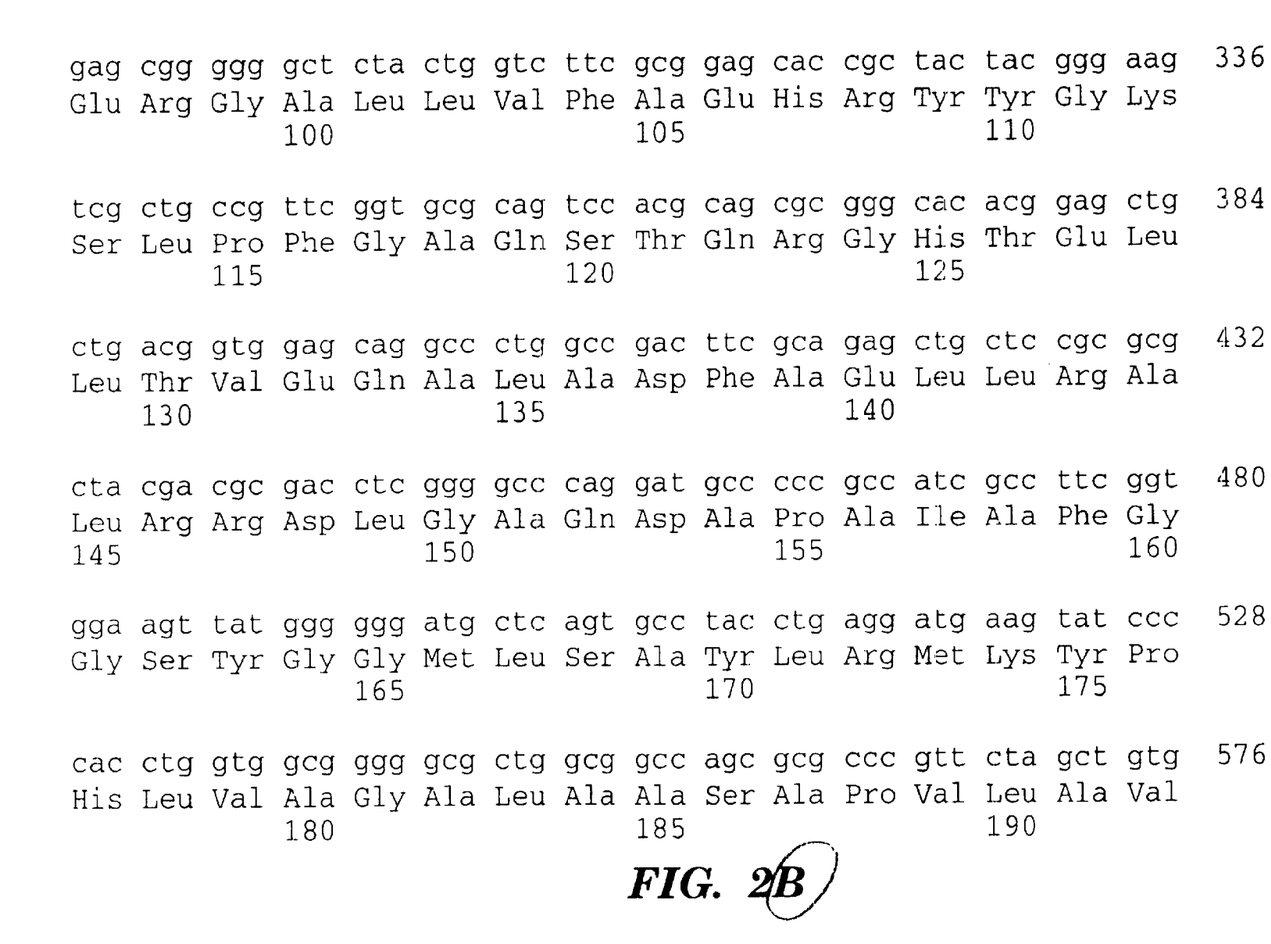
Figure 2C:
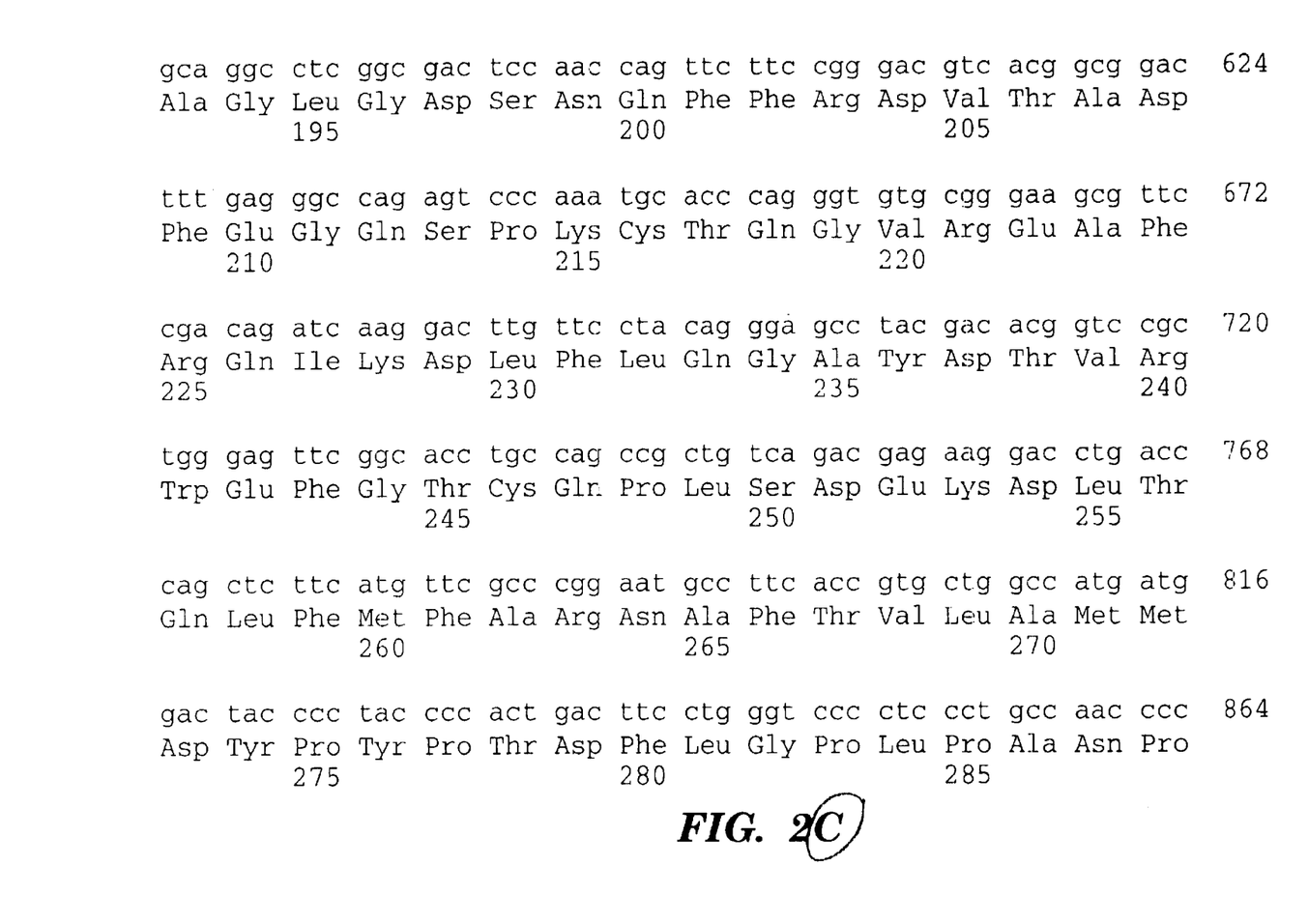
Figure 2D:
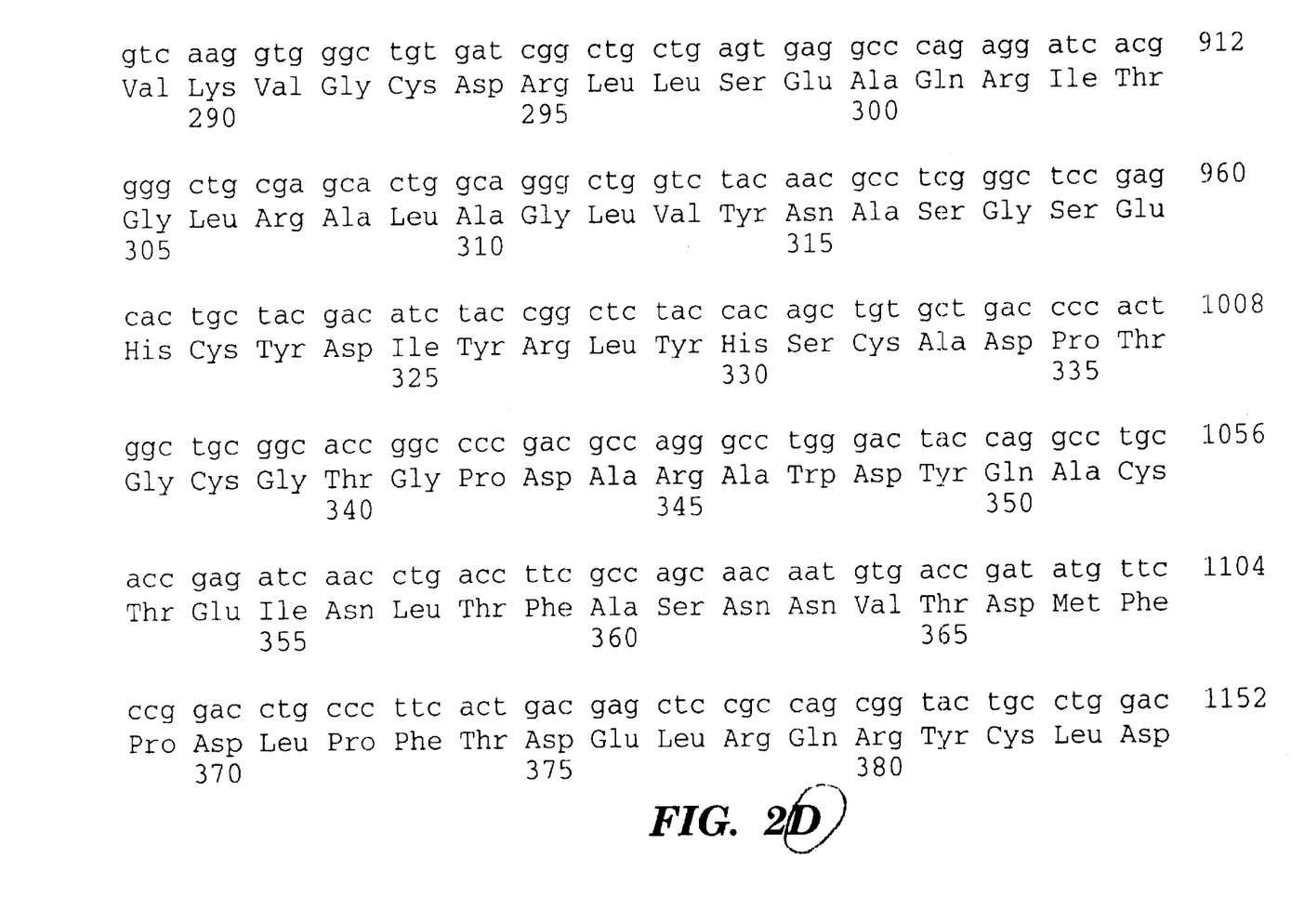
Figure 2E:
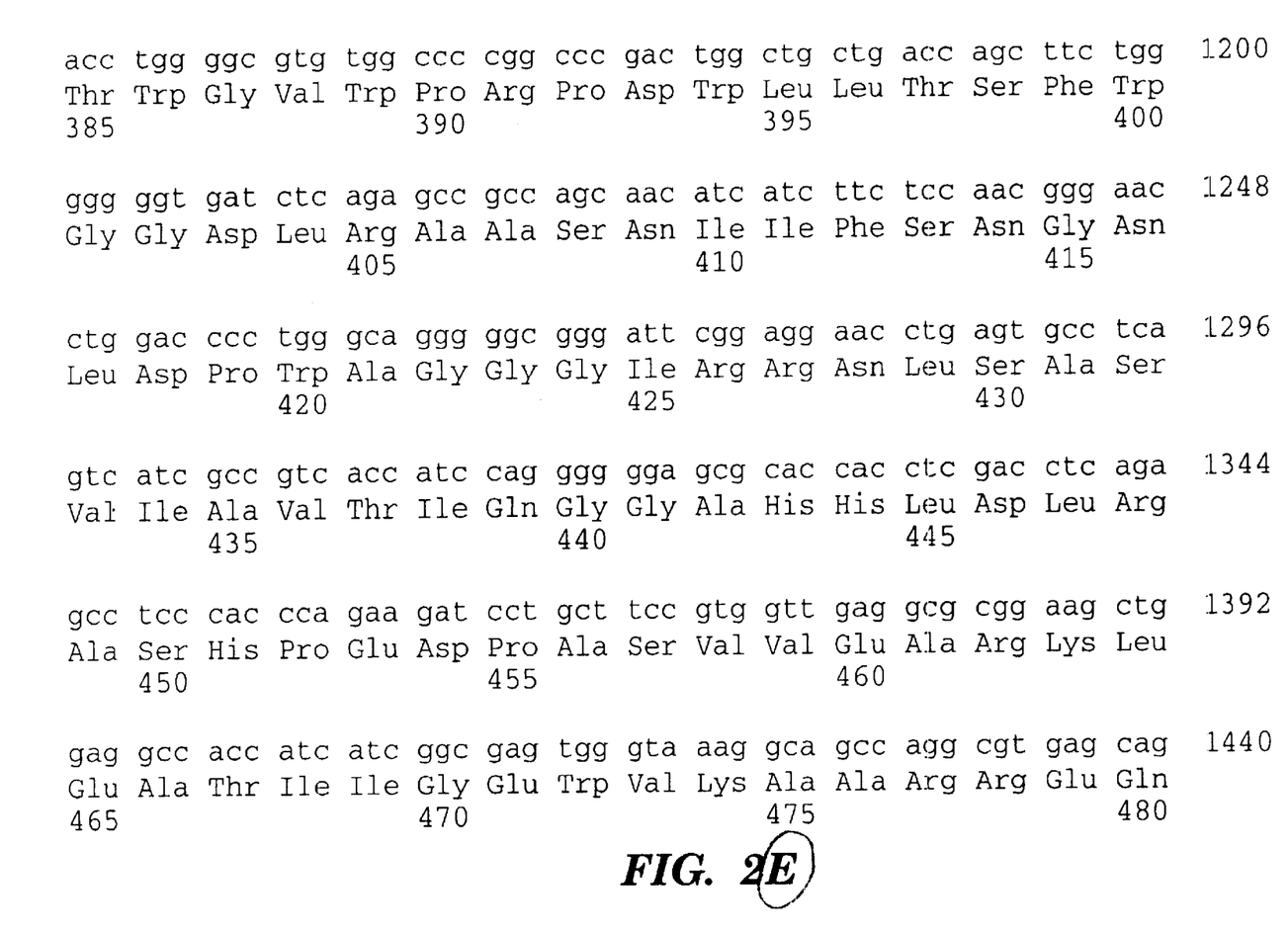
Figure 2F:
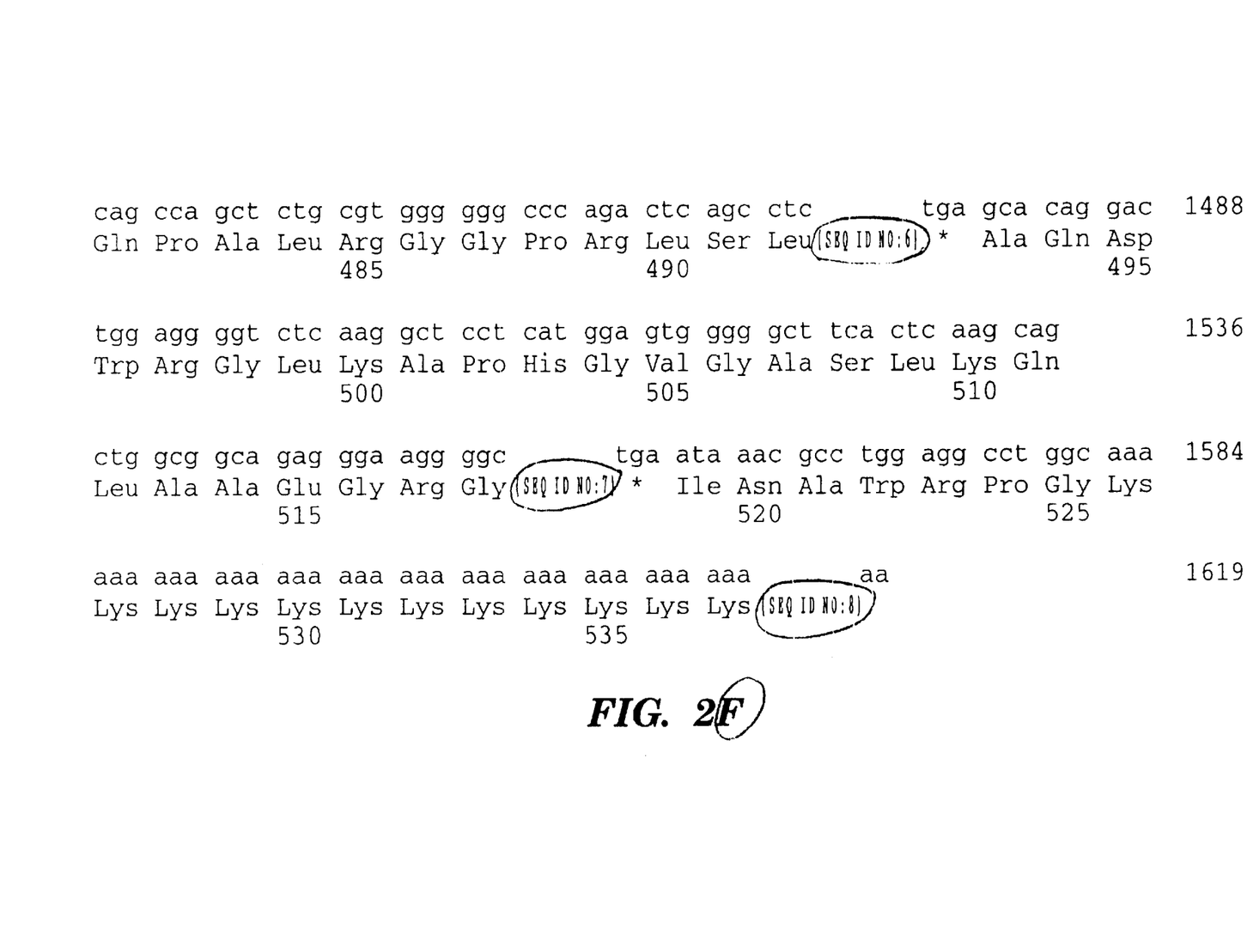

The sequences of four peptides of a QPP tryptic digest are shown in FIG. 1. Peptide GT148 (SEQ ID NO 1) is 13 residues long and has some homology to residues 281–293 of human prolylcarboxypeptidase (PCP). Peptide GT85 (SEQ ID NO 3) is 8 amino acids long and is identical to residues 17–24 of swine dipeptidyl peptidase II (DPPII). Based on these sequences, nucleic acid probes were designed to screen T-cell mRNA samples. The full length mRNA was isolated and sequenced; both the cDNA sequence and its predicted amino acid sequence are shown in FIG. 2 (SEQ ID NOs 5 and 6, respectively).

5. Expression of Recombinant QPP in Quiescent Fibroblasts Increases Cell Survival The role of QPP in protecting quiescent (non-cycling) cells from death was confirmed in fibroblasts transfected with a QPP transgene sequence using standard techniques. Expression of the recombinant QPP in serum-starved, $G_o$ phase fibroblasts inhibited apoptosis, as compared to non-QPP transfected fibroblasts.

Use as a Therapeutic

The demonstrated effect of QPP, protecting quiescent cells from apoptotic death, indicates that QPP can be used as a therapeutic to inhibit cell death, not only in T-cells, but also in other non-cycling cell types. For example, non-cycling cells of the central nervous system, such as neurons, will also exhibit a QPP-mediated protective effect against apoptosis. In addition to being non-cycling, neurons exhibit patterns of apoptosis analogous to T-cells, are susceptible to the same killer factors, and have a similar apoptotic signalling cascade. Furthermore, if neurons are denied the required trophic factors and cell-to-cell contact, they die by a mechanism similar to that exhibited in T-cells. All of the above factors are consistent with QPP exerting its effect in neurons as well as T-cells.

QPP-related therapy of non-cycling cells would be useful, for example, when a patient suffers from a condition, or is predisposed to suffer from a condition, associated with inappropriate cell death. For example, given that a number of human neurological disorders, as well as neurological traumatic injury or ischemia, are associated with apoptotic neuronal death, contacting the cells of the nervous system with QPP, or a compound which enhances the QPP effect, will be effective in treating patients suffering from such conditions. In particular, disorders or conditions that may be treated include, without limitation, Alzheimer's disease, Huntington's disease, Parkinson's disease, spinal muscular dystrophy ALS, multiple sclerosis, epilepsy, or stroke, as well as spinal cord injury. QPP or an agonist can also be administered therapeutically to patients in need of immune system enhancement, for example, to protect important T-cells such as CD4+ cells. Patients which would benefit from this treatment include AIDS patients threatened with reduced CD4+ cell counts and cancer patients with suppressed immune function as a result of their disease, chemotherapy, and/or radiation therapy.

Conversely, inhibitors of QPP can also be used to increase apoptotic death of non-cycling cells. Such therapy may be useful, for example, to kill T-cells, when an immunomodulating drug is needed for the treatment of allograft rejection, graft-versus-host disease, or auto-immune diseases such as rheumatoid arthritis.

Use as a Target for Screening

As briefly noted above, QPP-related therapy can take the form of administering compounds which either activate or inhibit the QPP effect. Such compounds can be identified using QPP as a target in screening assays. Compounds that enhance the QPP effect could act by either increasing QPP enzymatic activity or increasing QPP expression. Compounds that inhibit QPP action, on the other hand, could inhibit QPP enzymatic activity or inhibit QPP expression.

To screen for QPP enzymatic activity, any QPP substrate which contains proline in the penultimate position can be used. For example, the substrate AlaProAFC can be used in a fluorescent cleavage assay. Alternatively, a colorimetric assay can be carried out using as a substrate Gly-Pro-pNA as a substrate. The choice of terminal amino acid is not critical, provided that the substrate contain a free terminal amino group.

A fluorescence assay can be used, for example, which employs a fluorescence spectrometer for excitation at 400 nm and emission at 505 nm. The spectrometer is calibrated for fluorescence intensity of 0.000=10 mM HEPES, pH 7.4; and fluorescence intensity of 1.000=10 Mm HEPES, 1 M AFC.

To carry out the assay, between 10 and 100 $\mu$l of purified QPP enzyme, is diluted to 1 ml with 10 mM HEPES, pH 7.4, containing 10 mM Ala-Pro-AFC. At least one extract/substrate sample is run without test compound, to provide a standard for comparison with the test sample.

In the test samples, multiple samples are run containing varying concentrations, down to $10^{-8}$M, of the test compound. The sample (with or without test compound) is placed in a cuvette, and inserted into a fluorescent spectrometer. Enzymatic activity is measured as the accumulation of fluorescence intensity (i.e., substrate cleavage product) over a period of 1 min. A compound is identified as a QPP modulator if fluorescence is changed from the control value as a result of the presence of the compound.

Candidate compounds which modulate QPP activity in vitro can be tested for efficaciousness in secondary cell-based assays. Such assays provide relevant information regarding whether the candidate compound can cross the cell membrane, and produce an intracellular effect.

Cultures of cells are easily prepared for use in apoptosis assays by standard methods known in the art. For example, methods for isolating neurons can be found in Slack, R. S., et al., *J. Cell Biol.*, 135:1085, (1996); Belliveau, D. J., et al., *J. Cell Biol.*, 136:375 (1997); Brewer at al., *Nature* 363:265–266 (1993); or Henderson et al., *Nature* 363:266–267 (1993). After establishment of a healthy neuron culture, neurons can be induced to undergo apoptosis by exposure to any one of many well-characterized stimuli including NGF or BDNF withdrawal, serum withdrawal, exposure to hypoxic conditions, or the addition of chemicals that induce apoptosis, such as staurosporine or glutamate (see e.g., Koh et al., *Exp. Neurol.*, 135:153–159 (1995); MacManus et al., *Exp. Cell Res.*, 223:310–320, (1997)).

Compounds can also be screened for their effect on QPP gene expression. To screen for such compounds, QPP mRNA levels can be measured in cells which endogenously express QPP, for example, T-cells or neurons, or in cells transfected with QPP's upstream regulators operably linked to either its own QPP coding sequence or a reporter gene. Those compounds identified as increasing or decreasing QPP mRNA levels could increase or decrease the cellular QPP effect.

Proceeding to the next step, candidate compounds that modulate QPP activity or expression in cultured cells can be tested in animal models that are relevant to the disease condition of interest. Under some circumstances, such as the development of treatments for neurodegenerative conditions, the candidate compounds may be further modified to enhance their diffusion or transport across the blood-brain barrier. Particularly useful animal models include, without limitation, Parkinson's disease (PD) rat models, which are established by injecting the catecholamine-specific neurotoxin, 6-hydroxydopamine (6-OHDA), into the medial forebrain bundle or the substantia nigra pars compact to achieve a rapid degeneration of the nigrostriatal pathway, or into the striatum to achieve progressive degeneration, as has been described (see, for example Gerlach and Riederer, *J. Neural. Transm.* 103: 987–1041, 1996; Bernard et al., *J. Comp. Neurol.* 368: 553–568, 1996; Asada et al., *Ex. Neurol.* 139: 173–187, 1996). Alternatively, rats may be rendered "epileptic" (i.e., induced to suffer brain seizures which often result in neuronal cell death) by administration of a variety of compounds including intravenous injection of bicuculline (Blennow et al., *J. Cereb. Blood Flow Metab.* 5: 439–445, 1995). Furthermore, apoptosis may be induced by axotomy, ischemia, or traumatic insult to induce spinal cord injury, as described by Liu et al. (*J. Neuroscience* 17:5395–5406, 1997).

Test Compounds

In general, drugs for prevention or treatment of a condition related to inappropriate cell death, which function by altering the expression of QPP or its biological activity, are identified from libraries of natural products or synthetic (or semi-synthetic) extracts or chemical libraries according to methods known in the art. Examples of such extracts or compounds include, but are not limited to, plant-fungal-, prokaryotic- or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Libraries of genomic DNA or cDNA may be generated by standard techniques (see, e.g., Ausubel et al., supra) and are also commercially available (Clontech Laboratories Inc., Palo Alto, Calif.). Nucleic acid libraries used to screen for compounds that alter QPP gene expression or QPP enzymatic activity are not limited to the species from which the QPP gene or protein is derived. For example, a Xenopus cDNA may be found to encode a protein that alters human QPP gene expression or alters human QPP enzymatic activity.

Synthetic compound libraries are commercially available from Brandon Associates (Merrimack, N.H.) and Aldrich Chemical (Milwaukee, Wis.). Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are produced, if desired, according to methods known in the art, e.g., by standard extraction and fractionation methods.

In addition, methods for dereplication (e.g., taxonomic dereplication, biological dereplication, and chemical dereplication, or any combination thereof) or the elimination of replicates or repeats of materials already known for their therapeutic activities for neuroendocrine or pituitary disorders can be employed.

When a crude extract is found to modulate QPP's effect, further fractionation of the positive lead extract is necessary to isolate chemical constituents responsible. Thus, the goal of the extraction, fractionation, and purification process is the characterization and identification of a chemical entity within the crude extract having QPP-modulating activities. The same assays described herein for the detection of activities in mixtures of compounds can be used to purify the active component and to test derivatives thereof. Methods of fractionation and purification of such heterogenous extracts are known in the art. If desired, compounds shown to be useful agents for treatment are chemically modified according to methods known in the art.

Sources of QPP

QPP can be obtained by purification from human lymphocytes, as described herein, or from other QPP-expressing cells. Alternatively, the enzyme can be produced recombinantly using known techniques e.g., expression of the QPP coding sequence in mammalian cells such as Chinese hamster ovary cells.

Administration

QPP or the compounds which modulate the QPP effect may be administered by any appropriate route. For example, administration may be parenteral, intravenous, intra-arterial, subcutaneous, intramuscular, intracranial, intraorbital, ophthalmic, intraventricular, intracapsular, intraspinal, intracisternal, intraperitoneal, intranasal, aerosol, by suppositories, or oral administration.

Therapeutic formulations may be in the form of liquid solutions or suspensions; for oral administration, formulations may be in the form of tablets or capsules; and for intranasal formulations, in the form of powders, nasal drops, or aerosols.

Methods well known in the art for making formulations are found, for example, in "Remington's Pharmaceutical Sciences." Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycholate and deoxycholate, or may be oily solutions for administration in the form of nasal drops, or as a gel. The concentration of QPP in the formulation will vary depending upon a number of factors, including the dosage of the drug to be administered, and the route of administration.

The formulations can be administered to human patients in therapeutically effective amounts (e.g., amounts which prevent, eliminate, or reduce the pathological condition) to provide therapy for the disorders described above. Typical dose ranges are from about 0.1 $\mu$g/kg to about 1 g/kg of body weight per day. The preferred dosage of drug to be administered is likely to depend on such variables as the type and extent of the disorder, the overall health status of the particular patient, the formulation of the compound excipients, and its route of administration.

Antibodies Directed Against QPP

The QPP amino acid sequence, or fragments thereof, can be used to generate polyclonal or monoclonal antibodies specific for QPP, using conventional techniques. Such antibodies can be used in the above-described screening assays, and in any of the many known conventional immunoassay formats to measure QPP levels in biological samples, e.g., samples of peripheral blood lymphocytes. A decreased level of lymphocyte QPP, as determined in such assays, is indicative of immune dysfunction in the patient from whom the sample was obtained.

Other Embodiments

All publications and patent applications mentioned in this specification are herein incorporated by reference.

While the invention has been described in connection with specific embodiments, it will be understood that it is capable of further modifications. Therefore, this application is intended to cover any variations, uses, or adaptations of the invention that follow, in general, the principles of the invention, including departures from the present disclosure that come within known or customary practice within the art.

Other embodiments are within the claims.

What is claimed is:

1. A substantially pure nucleic acid molecule encoding a QPP polypeptide, wherein said polypeptide comprises the amino acid sequence of SEQ ID NO: 6.

* * * * *

UNITED STATES PATENT AND TRADEMARK OFFICE
CERTIFICATE OF CORRECTION

PATENT NO. : 6,706,868 B2  
DATED : March 16, 2004  
INVENTOR(S) : Brigitte T. Huber and Robert H. Underwood Page 1 of 1

It is certified that error appears in the above-identified patent and that said Letters Patent is hereby corrected as shown below:

Column 1,
Line 1, after the title and before "CROSS REFERENCE TO RELATED APPLICATION", please add the following:

-- Government Support

This invention was made with government support under AI36696 and AI43469 awarded by the National Institutes of Health. The government has certain rights in the invention. --

Signed and Sealed this

Thirtieth Day of November, 2004

JON W. DUDAS
*Director of the United States Patent and Trademark Office*